United States Patent
Aberg

(12) 
(10) Patent No.: US 6,310,103 B1
(45) Date of Patent: Oct. 30, 2001

(54) S(−)-TOLTERODINE IN THE TREATMENT OF URINARY AND GASTROINTESTINAL DISORDERS

(75) Inventor: Gunnar Aberg, Sarasota, FL (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 09/230,115

(22) PCT Filed: Jul. 14, 1997

(86) PCT No.: PCT/US97/12155

§ 371 Date: Jan. 11, 1999

§ 102(e) Date: Jan. 11, 1999

(87) PCT Pub. No.: WO98/03067

PCT Pub. Date: Jan. 29, 1998

Related U.S. Application Data

(60) Provisional application No. 60/020,995, filed on Jul. 19, 1996.

(51) Int. Cl.⁷ .................................................. A61K 31/05
(52) U.S. Cl. ........................... 514/741; 424/45; 424/436; 424/443; 424/449; 424/464; 424/489; 564/315; 564/316
(58) Field of Search .............................. 424/45, 489, 436, 424/443, 449, 464; 514/741; 564/315, 316

(56) References Cited

FOREIGN PATENT DOCUMENTS

| 0 325 571 | 7/1989 | (EP) . |
|---|---|---|
| 9829402 | * 7/1998 | (WO) . |
| 12070 | * 3/2000 | (WO) . |
| 27364 | * 5/2000 | (WO) . |

OTHER PUBLICATIONS

Nilvebrant, L. Tolterodine—A New Bladder Selective Muscarinic Receptor Antagonist: Preclinical Pharmacological Data. Life Sciences. 1977, vol. 60, pp. 1129–1136.

Nilvebrant, L. Tolterodine—A New Bladder Selective Antimuscarinic Agent. Eur. J. Pharmacol. 1977, vol. 327, pp. 195–207.

* cited by examiner

Primary Examiner—Raj Bawa
(74) Attorney, Agent, or Firm—Nields & Lemack

(57) ABSTRACT

The S-isomer of a compound represented by the following formula:

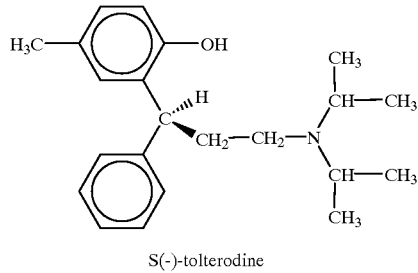

S(−)-tolterodine and pharmaceutically acceptable salts thereof is disclosed as being useful for treating urinary disorders, including urinary incontinence, and gastrointestinal disorders, including gastrointestinal hyperativity.

12 Claims, No Drawings

S(-)-TOLTERODINE IN THE TREATMENT OF URINARY AND GASTROINTESTINAL DISORDERS

This application claims benefit of Prov. No. 60/020,995 filed Jul. 19, 1996.

FIELD OF THE INVENTION

This invention relates to a compound named S(-)-tolterodine and having the formula:

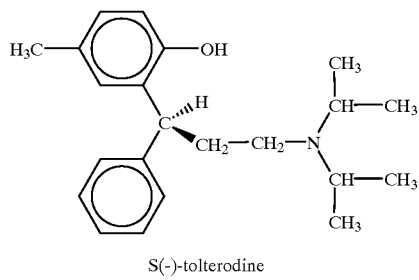

S(-)-tolterodine

Specifically, the invention relates to processes for preparing S-tolterodine, to a method for treating urinary disorders, including urinary incontinence and a method for treating gastrointestinal disorders, including gastrointestinal hyperactivity, using the compound S-tolterodine and to pharmaceutical compositions containing S-tolterodine.

The generic name TOLTERODINE (CAS-124937-51-1; INN) refers to the R-enantiomer of the drug. In this document, the racemate and the optically active isomers of the compound are referred to as RS-tolterodine (or RS-TOL), S-tolterodine (or S-TOL), and R-tolterodine (or R-TOL).

BACKGROUND OF THE INVENTION

R-tolterodine has been shown to reduce bladder pressure in cats and is presently undergoing clinical testing for inhibitory activity in patients suffering from detrusor overactivity (urinary incontinence). R-TOL exerts a spasmolytic effect on bladder smooth muscle by inhibiting the action of acetylcholine on smooth muscle. R-TOL is selective for muscarinic receptors over nicotinic receptors and as a result, no blocking effects are observed at skeletal neuromuscular junctions. Like all other antimuscarinic compounds, R-TOL causes dry mouth, blurry vision, tachycardia and possibly also memory impairment.

R-TOL relaxes urinary bladder smooth muscle and in animals with conditions characterized by increased bladder contractions, cystometric studies have demonstrated that R-TOL has beneficial effects. R-TOL may therefore be useful in the treatment and prevention of incontinency and frequent voluntary urination in patients. The efficacy of R-TOL in the bladder has been attributed to its antimuscarinic effects on the detrusor muscle. Because of its antimuscarinic activity, mydriasis (dilated pupils), xerostomia (dry mouth), tachycardia (fast heart beats) and impaired normal urinary voiding, which mechanisms all involve muscarinic cholinergic receptors, are obvious and reported side effects for R-TOL (Ekström et al., J. Urol. 1995, Suppl.4: 394A and Stahl et al. 1995. Neurourol Urodyn 14:647–655).

Pharmacological studies of the individual enantiomers of tolterodine have now been performed and have suggested that the R-TOL indeed is the efficacious enantiomer on muscarinic receptors. Thus, it was concluded that the cholinergic antagonism of racemic tolterodine (RS-TOL) could be attributed mainly to the activity of R-TOL. The rank order of potency of racemic tolterodine and its enantiomers for antimuscarinic activity is: R-TOL was greater or equal to RS-TOL, which was much greater than S-TOL, with S-TOL being approximately one or more orders of magnitude less potent than R-TOL.

SUMMARY OF THE INVENTION

It has now unexpectedly been found that S-TOL has outstanding non-cholinergic spasmolytic activities, while being practically devoid of anticholinergic activity. It has furthermore unexpectedly been found that S-TOL provides weak sedative effects. S-TOL therefore will offer superior treatment for urinary disorders, including urinary incontinence and for gastrointestinal disorders, including gastrointestinal hyperactivity, while being devoid of the anticholinergic side effects that reside in R-TOL.

While the optically pure R-TOL provides medical treatment in patients with urinary incontinence that arises from one single cause, namely muscarinic hyperactivity, it was found that the optically pure S-TOL provides spasmolytic activity against urinary and intestinal spasms that arise from various mechanisms. S-TOL is particularly useful in patients where urinary incontinence is caused by non-cholinergic mechanisms or in patients, where antimuscarinic side effects are not acceptable (for example in the elderly, where antimuscarinic side effects have unacceptable effects on memory). Non-cholinergic spasmogenic mechanisms include but are not limited to scars (i.e. from childberth or surgical interventions) causing detrusor pacemaker activity, release of thromboxane, release of platelet activating factor and other non-muscarinic spasmogens.

Chemically, S-TOL is S(-)-2-[α[2-(diisopropylamino) ethyl] benzyl]-p-cresol.

The active compound of this invention is S-TOL. The synthetic preparation is described in European Pat. Appl. EP 325571 A1, the disclosures of which are hereby incorporated by reference.

Alternatively, S-TOL can be prepared by stereoselective synthesis, using (other) chiral templates.

Alternatively, S-TOL can be obtained by the resolution of RS-TOL using conventional means such as fractional crystallization of diastereomeric salts with chiral acids. Other standard methods of resolution known to those skilled in the art, include, but are not limited to, crystallization and chromatography on a chiral substrate and can also be used.

The magnitude of a prophylactic or therapeutic dose of S-TOL in the acute or chronic management of disease will vary with the severity and nature of the condition to be treated and the route of administration. The dose and the frequency of the dosing will also vary according to the age, body weight and response of the individual patient. In general, the total daily dose range for S-TOL for the conditions described herein is from about 0.5 mg to about 100 mg in single or divided doses, preferably in divided doses. In managing the patient, the therapy should be initiated at a lower dose, perhaps at about 0.5 mg to about 25 mg, and may be increased up to about 200 mg depending on the patient's global response. It is further recommended that patients over 65 years and those with impaired renal or hepatic function initially receive low doses and that they be titrated based on individual response(s) and plasma drug level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat the disorder but insufficient to cause adverse effects" are encompassed by the above-described dosage amounts and dose frequency schedule.

Any suitable route of administration may be employed for providing the patient with an effective dosage of S-TOL. For example, oral, sublingual, parental (i.e. subcutaneous, intramuscular, intravenous, etc.), transdermal, vaginal, aerosol and like forms of administration may be employed. Additionally, the drug may be administered directly into the bladder, as described for oxybutynin by Massad et al. [*J. Urol* 148. 595–597 (1992)] or rectally directly into the gastrointestinal canal as known in the art. Dosage forms include tablets, troches, dispersions, suspensions, solutions, capsules, suppositories, microencapsulated systems, slow-release and controlled release systems, transdermal delivery systems, and the like.

The pharmaceutical compositions of the present invention comprise of S-TOL as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The hydrochloride is particularly preferred.

The compositions of the present invention include suspensions, solutions, elixirs or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations.

Because of their ease of administration, tablets and capsules represent the more advantageous oral dosage unit forms, in which case solid pharmaceutical carriers are employed. If desired, tablets may be coated by standard aqueous or nonaqueous techniques.

In addition to the common dosage forms set out above, the compounds of the present invention may also be administered by controlled release means and delivery devices such as those described in U.S. Pat. Nos. 3,845,770; 3,916,899; 3,536,809; 3,598,123; and 4,008,719, and PCT application WO92/20377, the disclosures of which are hereby incorporated by reference.

Pharmaceutical compositions of the present invention suitable for oral administration may be presented as discrete unit dosage forms such as capsules, cachets, suppositories, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation, just as is known for the racemic mixture.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. All of the foregoing techniques are well know to persons of skill in the pharmaceutical art. Each tablet may contain from about 0.5 mg to about 25 mg of the active ingredient.

EXAMPLES

EXAMPLES
Example 1
ORAL UNIT DOSAGE FORMULATION

| Tablets:<br>Ingredients | per tablet | per batch of<br>10.000 tablets |
|---|---|---|
| S-TOL | 5 mg | 50 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

The S-TOL is blended with lactose and cellulose until a uniform blend is formed. The lake is added and further blended. Finally, the calcium stearate is blended in, and the resulting mixture is compressed into tablets using a 9/32 inch (7 mm) shallow concave punch. Tablets of other strengths may be prepared by altering the ration of active ingredient to the excipients or to the final weight of the tablet.

Example 2

Pharmacological Studies of S-TOL, RS-TOL or R-TOL

1. Ligand Binding Studies: Muscarinic Receptors

The experimants are carried out on membranes prepared from SF9 cells infected with baculovirus to express human recombinant muscarinic receptor subtypes. After incubation with the test article and the proper radioligand and washing, bound radioactivity is determined with a liquid scintillation counter, using a commercial scintillation cocktail. The specific radioligand binding to each receptor is defined as the difference between total binding and nonspecific binding determined in the presence of an excess of unlabelled ligand. $IC_{50}$ values (concentrations required to inhibit 59% of specific binding) are determined by non linear regression analysis of the competition curves. These parameters are obtained by curve fitting using Sigmaplot™ software.

2. Functional Characterization of Antimuscarinic/Antispasmodic Activity

Bladder and intestinal smooth muscle strips. Experiments are performed using methods similar to those described by Kachur et al, 1988 and Noronha-Blob and Kachur, 1991. Strips of tissue (approximately 10 mm long and 1.5 mm wide) are removed from the body of the urinary bladder of male Hartley guinea pigs weighing 400–600 g. Preparations of the longitudinal smooth muscle of the colon of guinea pigs are prepared as known in the art (Acta Physiol Scand 64: 15–27, 1965). The tissues are suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7, or of a similar composition. They are maintained at 37.5 C. Contractions are recorded with isometric transducers (Model FT-10) on an ink-writing polygraph.

In each experiment up to seven strips are removed from a single animal, suspended in tissue chambers and allowed to equilibrate with the bathing solution for one hour before proceeding with the experiment.

Contractions induced by carbachol. One series of experiments focuses on the anticholinergic actions of S-TOL, RS-TOL or R-TOL. In these experiments, in order to assess the viability of each tissue and to serve as a frame of reference, contractions of each strip of tissue are recorded initially in response to exposure to tissue medium in which the NaCl was replaced by KCl to yield a concentration of 137.7 mM KCl in the medium. This is followed by return to the standard medium, and then by exposures to progressively in creasing concentrations of carbachol, with separate exposures to each concentration only until the peak response has been recorded. Then, leaving one strip untreated and/or one strip exposed to the test solution to serve as control tissue(s), the remaining strips each are exposed for one hour to one concentration of an antagonist. Finally, the responses to increasing concentrations of carbachol followed by exposure to 137.7 mM KCL are recorded a second time.

Contractions induced by hig potassium concentration. A second series of experiments focuses on the spasmolytic action of the substances being studied against high concentrations of $K^+$. Contractions in response to sequentially increasing the concentration of potassium in the medium are recorded.

Contractions induced by other spasmogens. A third series of experiments focuses on spasmolytic activities against other spasmogens. The contractions are recorded in response to sequentially increasing the concentration of such spasmogens in the medium.

Data analysis. To determine whether antagonists decrease the peak response to agonists, the peak tension developed by each strip during the second set of determinations is expressed as a percent of the peak tension developed during the first concentration-effect determination. Then, for each antagonist the resultant data are analyzed for treatment-related differences by one-way analysis of variance (ANOVA). Since only one concentration of antagonist is studied in each strip of bladder, a modified procedure is used to estimate the pA2 and slope of the Schild regression. First, the concentrations of agonist producing a half-maximal response (the $EC_{50}$) is estimated for each strip from the second set of concentration-effect data. The $EC_{50}$ is obtained from linear regression lines fit to the logarithm of the concentration of drug and the responses bracketing the half maximum level of response. For each drug-treated strip, a "concentration ratio" (CR) is calculated as the ratio of the $EC_{50}$ of the treated tissue divided by the $EC_{50}$ (of the untreated tissue. For each experiment where two or more strips are exposed to the same chemical but at different concentrations, the logarithm of this ratio minus one [i.e. log (CR-1)] is plotted against the logarithm of the concentration of antagonist to which the strip had been exposed to produce "Schild plots". A regression analysis relating log(CR-1) to the logarithm of the concentration of the antagonist is employed to estimate the pA2 and the slope of the regression line. Finally, experiments are grouped by chemical and the mean ±S.E.M. of the pA2 and slope are calculated.

Since S-TOL exhibits significantly decreased anticholinergic side effects as compared with the corresponding R-isomer and racemate, administration of S-tolterodine will allow avoidance of parasympathec cardiovascular side effects (i.e. tachycardia etc.) and other parasympathetic side effects (i.e. dry mouth, blurry vision, inhibition of normal urinary voiding mechanisms etc.), and the avoidance of memory loss that arise from the anticholinergic action of R-TOL. It is now therefore concluded that S-TOL is an effective medicament for the treatment of urinary voiding disorders, including urinary incontinence, and for the treatment of gastrointestinal disorders, including gastrointestinal hyperactivity in humans with greatly reduced side effects over the corresponding racemate or the pure R-enantiomer.

What is claimed is:

1. A method for treating urinary incontinence incontinence, while reducing concomitant liability of adverse effects associated with racemic tolterodine or the R-enantiomer of tolterodine, which comprises administering to a mammal in need of such treatment a therapeutically effective amount of S(−)-2-[α-[2-(diisopropylamino)ethyl] benzyl]-p-cresol or a, pharmaceutically acceptable salt thereof, substantially free of its R enantiomer.

2. A method for treating gastrointestinal hyperactivity, while reducing concomitant liability of adverse effects associated with racemic tolterodine or the R-enantiomer of tolterodine, which comprises administering to a mammal in need of such treatment a therapeutically effective amount of S(−)-2-[α-[2-(diisopropylamino)ethyl]benzyl]-p-cresol or a pharmaceutically acceptable salt thereof, substantially free of its R enantiomer.

3. The method of claim 1 wherein the amount of S(−)-2-[α-[2-(diisopropylamino)ethyl]benzyl]-p-cresol or a pharmaceutically acceptable salt thereof is administered from about 0.5 mg to about 200 mg per day.

4. The method of claim 2 wherein the amount of S(−)-2-[α-[2-(diisopropylamino)ethyl]benzyl]-p-cresol or a pharmaceutically iacceptable salt thereof is administered from about 0.5 mg to about 200 mg per day.

5. The method according to claim 1 wherein S(−)-2-[α-[2-(diisopropylamino)ethyl]benzyl]-p-cresol or a pharmaceutically acceptable salt thereof, is administered orally.

6. The method according to claim 2 wherein S(−)-2-[α-[2-(diisopropylamino)ethyl]benzyl]-p-cresol, or a pharmaceutically acceptable salt thereof, is administered orally.

7. The method according to claim 1 wherein S(−)-2-[α-[2-(diisopropylamino)ethyl]benzyl]-p-cresol, or a pharmaceutically acceptable salt thereof, is administered orally in an extended release formulation.

8. The method according to claim 2 wherein S(−)-2-[α-[2-(diisopropylamino)ethyl]benzyl]-p-cresol, or a pharmaceutically acceptable salt thereof, is administered orally in an extended release formulation.

9. The method according to claim 1 wherein S(−)-2-[α-[2-(diisopropylamino)ethyl]benzyl]-p-cresol, or a pharmaceutically acceptable salt thereof, is administered transdermally.

10. The method according to claim 2 wherein S(−)-2-[α-[2-(diisopropylamino)ethyl]benzyl]-p-cresol, or a pharmaceutically acceptable salt thereof, is administered transdermally.

11. The method of claim 1 wherein S(−)-2-[α-[2-(diisopropylamino)ethyl]benzyl]-p-cresol or a pharmaceutically acceptable salt thereof is administered by a mode of administration selected from the group consisting of inhalation, parenteral, transdermal, rectal, sublingual and oral administration.

12. The method of claim 2 wherein S(−)-2-[α-[2-(diisopropylamino)ethyl]benzyl]-p-cresol or a pharmaceutically acceptable salt thereof is administered by a mode of administration selected from the group consisting of inhalation, parenteral, transdermal, rectal, sublingual and oral administration.

* * * * *